US009744056B2

(12) United States Patent
Kuiken et al.

(10) Patent No.: US 9,744,056 B2
(45) Date of Patent: Aug. 29, 2017

(54) MAGNETIC ELECTRICAL CONNECTOR FOR ASSISTIVE DEVICES

(71) Applicant: Rehabilitation Institute of Chicago, Chicago, IL (US)

(72) Inventors: Todd Kuiken, Oak Park, IL (US); Timothy Reissman, Chicago, IL (US); Elizabeth Halsne, Chicago, IL (US); Robert Lipschutz, Naperville, IL (US)

(73) Assignee: REHABILITATION INSTITUTE OF CHICAGO, Chicago, IL (US)

( * ) Notice: Subject to any disclaimer, the term of this patent is extended or adjusted under 35 U.S.C. 154(b) by 21 days.

(21) Appl. No.: 14/453,278

(22) Filed: Aug. 6, 2014

(65) Prior Publication Data

US 2016/0038314 A1 Feb. 11, 2016

(51) Int. Cl.
| | |
|---|---|
| *A61F 2/78* | (2006.01) |
| *A61F 2/80* | (2006.01) |
| *A61F 2/76* | (2006.01) |
| *A61B 5/0488* | (2006.01) |
| *A61B 5/0492* | (2006.01) |
| *A61F 2/72* | (2006.01) |
| *A61F 2/50* | (2006.01) |
| *A61F 2/68* | (2006.01) |

(52) U.S. Cl.
CPC ............... *A61F 2/80* (2013.01); *A61F 2/76* (2013.01); *A61F 2/7812* (2013.01); *A61B 5/0492* (2013.01); *A61B 5/04888* (2013.01); *A61F 2/72* (2013.01); *A61F 2002/5007* (2013.01); *A61F 2002/5072* (2013.01); *A61F 2002/5083* (2013.01); *A61F 2002/5089* (2013.01); *A61F 2002/6863* (2013.01); *A61F 2002/7875* (2013.01); *A61F 2002/7887* (2013.01); *A61F 2220/0008* (2013.01)

(58) Field of Classification Search
CPC ....... A61F 2/78; A61F 2/80; A61F 2002/0008
See application file for complete search history.

(56) References Cited

U.S. PATENT DOCUMENTS

| | | | |
|---|---|---|---|
| 1,350,518 | A | 8/1920 | Prisbrey |
| 3,140,712 | A | 7/1964 | Hunter |
| 4,004,298 | A | 1/1977 | Freed |
| 4,024,588 | A | 5/1977 | Janssen et al. |
| 4,112,941 | A | 9/1978 | Larimore |
| 4,536,898 | A | 8/1985 | Palfray |
| 4,743,264 | A | 5/1988 | Sherva-Parker |
| 4,908,037 | A | 3/1990 | Ross |
| 5,378,161 | A | 1/1995 | Loder |

(Continued)

OTHER PUBLICATIONS

PCT, Notification of Transmittal of the International Search Report and the Written Opinion of the International Searching Authority, or the Declaration, in application No. PCT/US15/43704, dated Oct. 29, 2015 (8 pages).

(Continued)

*Primary Examiner* — Bruce E Snow
(74) *Attorney, Agent, or Firm* — Benesch, Friedlander, Coplan & Aronoff LLP

(57) ABSTRACT

A magnetic and electrical interface that may be used with an assistive device. The interface comprises a proximal connector and a distal connector. The proximal connector may be attached to a liner for a residual limb and the distal connector may be attached to a hard socket or other aspect of an assistive device. Other aspects of and uses for the connector interface are also disclosed.

25 Claims, 6 Drawing Sheets

(56) References Cited

U.S. PATENT DOCUMENTS

| | | |
|---|---|---|
| 5,507,835 A | 4/1996 | Jore |
| 5,830,237 A | 11/1998 | Kania |
| 5,879,386 A | 3/1999 | Jore |
| 6,273,918 B1 | 8/2001 | Yuhasz et al. |
| 6,387,096 B1 | 5/2002 | Hyde, Jr. |
| 6,599,321 B2 | 7/2003 | Hyde, Jr. |
| 6,705,794 B2 | 3/2004 | Varner et al. |
| 7,033,400 B2 | 4/2006 | Currier |
| 7,144,179 B2 | 12/2006 | Varner et al. |
| 7,169,188 B2 | 1/2007 | Carstens |
| 7,325,996 B2 | 2/2008 | Varner et al. |
| 7,351,264 B2 | 4/2008 | Wilson |
| 7,427,297 B2 | 9/2008 | Patterson et al. |
| 7,618,435 B2 | 11/2009 | Opolski |
| 8,206,459 B1 | 6/2012 | Lock |
| 8,434,668 B2 | 5/2013 | Aleksov |
| 2002/0032484 A1 | 3/2002 | Hyde |
| 2003/0187510 A1 | 10/2003 | Hyde |
| 2003/0195633 A1 | 10/2003 | Hyde |
| 2003/0236572 A1 | 12/2003 | Bertram |
| 2004/0028467 A1 | 2/2004 | Currier |
| 2005/0256589 A1 | 11/2005 | Slemker et al. |
| 2006/0096070 A1 | 5/2006 | Ishida |
| 2006/0282175 A1 | 12/2006 | Haines et al. |
| 2006/0293762 A1 | 12/2006 | Schulman et al. |
| 2007/0021841 A1 | 1/2007 | Al-Temen |
| 2007/0180858 A1 | 8/2007 | Wiseman |
| 2011/0264172 A1 | 10/2011 | Zimmerling |
| 2012/0296155 A1 | 11/2012 | Ball |
| 2013/0046394 A1 | 2/2013 | Lipschutz |
| 2013/0289743 A1 | 10/2013 | Abu |

OTHER PUBLICATIONS

Eshraghi, "Development and Evaluation of New Coupling System for Lower Limb Prosthese with Accoustic Alarm System," Scientific Reports, published Jul. 24, 2013, pp. 1-5.

MAGNETIC ELECTRICAL CONNECTOR FOR ASSISTIVE DEVICES

FEDERALLY SPONSORED RESEARCH OR DEVELOPMENT

This invention was made with government support under award W81XWH-11-1-0720 awarded by the U.S. Army. The government has certain rights in the invention.

RELATED APPLICATIONS

[Not Applicable]

MICROFICHE/COPYRIGHT REFERENCE

[Not Applicable]

FIELD OF THE INVENTION

The document relates generally to the field of prosthetic devices, and in particular, to the magnetic and electrical connection of different components of prosthetic devices.

BACKGROUND OF THE INVENTION

In the field of prosthetics and orthotics, artificial limbs can be used by people who have lost an arm, leg, hand or other portion of a limb. A person who is born without a limb, or who has lost a limb due to accident or disease, may use an artificial limb to perform tasks and activities of a human limb. Amputees may retain a portion of a limb known as a "residual limb." A prosthetist can create a plaster mold of the residual limb and use this mold to create a custom "hard socket" that is worn by the amputee. The prosthetist generally attaches the custom hard socket to the artificial limb using laminate or other means in the art at the distal end of the hard socket. The hard socket and the artificial limb are connected to make up a single piece of equipment. A prosthesis, orthosis, or exoskeleton is known as an "assistive device."

An amputee may put on (or "don") a prosthetic liner before donning the hard socket. A prosthetic liner fits in a hard socket like a sock fits in a shoe. The liner helps maintain a proper fit of the residual limb in the hard socket, reduces pressure points, reduces skin irritation and provides additional benefits. As such, for proper support of the artificial limb, the liner must fit well and be secured within the hard socket. Thus, a user of an artificial limb needs a way to easily attach and detach the hard socket/artificial limb component from the liner. When the attachment mechanism is inside the hard socket, the user cannot see or necessarily feel the attachment mechanism. Additionally, because a liner stretches when it is placed over a residual limb, it has a tension force that resists pulling in the distal direction and makes attachment to a hard socket more difficult for the amputee. An attachment mechanism that allows a simple attachment of the liner to the hard socket is needed.

Some artificial limbs are powered and can be controlled by a microprocessor. One such limb, known as a myoelectric prosthesis, uses its microprocessor to translate electrical signals from the user's remaining muscles into command signals that are transmitted to different components of the artificial limb. Myoelectric assistive devices generally require a system that allows for transmission of electrical signals from the user's muscles to the assistive device. One liner for myoelectric assistive devices is described in R. Lipschutz, D. Tkach, B. Lock, L. Hargrove, and T. Kuiken, Systems and Methods of Myoelectric Prosthesis Control, U.S. patent application Ser. No. 13/587,755, filed Aug. 16, 2012, which is incorporated by reference.

In the prior art, different prosthetic liner connectors are known. One such example of liner connectors are pin locks which involve the use of a threaded rod screwed, on the distal end, into an embedded female thread and mechanically locked on the other end into the prosthesis. The connector acts as a mechanical pin and can have different styles such as rastered, clutch, smooth and ball bearing. The pin provides purely a mechanical connection and does not pull in the liner within the prosthesis until it is already physically engaged. (The words "distal" and "proximal" are used to identify relative distance from the user. A "proximal" end of a component is located closer to the user, while a "distal" end of the component is located further from the user.)

Prior art attachment systems such as the Maglock (ST&G Corp., Brea, Calif.) or the MagnoFlex Lock (Ottobock, Germany) provide assisted donning and a mechanical attachment between the liner and a prosthesis, but the systems do not provide the electrical connectivity required by a myoelectric assistive device.

Furthermore, in the prior art, compliance components, such as washers, are not necessarily used to support two connecting magnets. If the compliance components oscillate 180 degrees out of phase, the oscillation may break the magnetic connection between the two magnets. If an electrical signal passes between the magnets, oscillation could similarly break the electrical connection and result in the loss of electrical signal.

BRIEF SUMMARY OF THE INVENTION

In one embodiment, a system for attaching an assistive device to a human limb is disclosed. The system comprises a liner having an opening for the insertion of a human limb, a proximal connector attached to the liner and a distal connector. The proximal connector has a proximal housing including a plurality of proximal magnets arranged on a proximal face. The distal connector has a distal housing including a plurality of distal magnets arranged on a distal face. At least one electrical signal that is representative of one or more human electromyography signals can be transmitted between the proximal connector and the distal connector via at least one of the plurality of proximal magnets and at least one of the plurality of distal magnets. The signal can be transmitted when the proximal connector and the distal connector are magnetically attached.

DETAILED DESCRIPTION OF THE INVENTION

Figure 1:
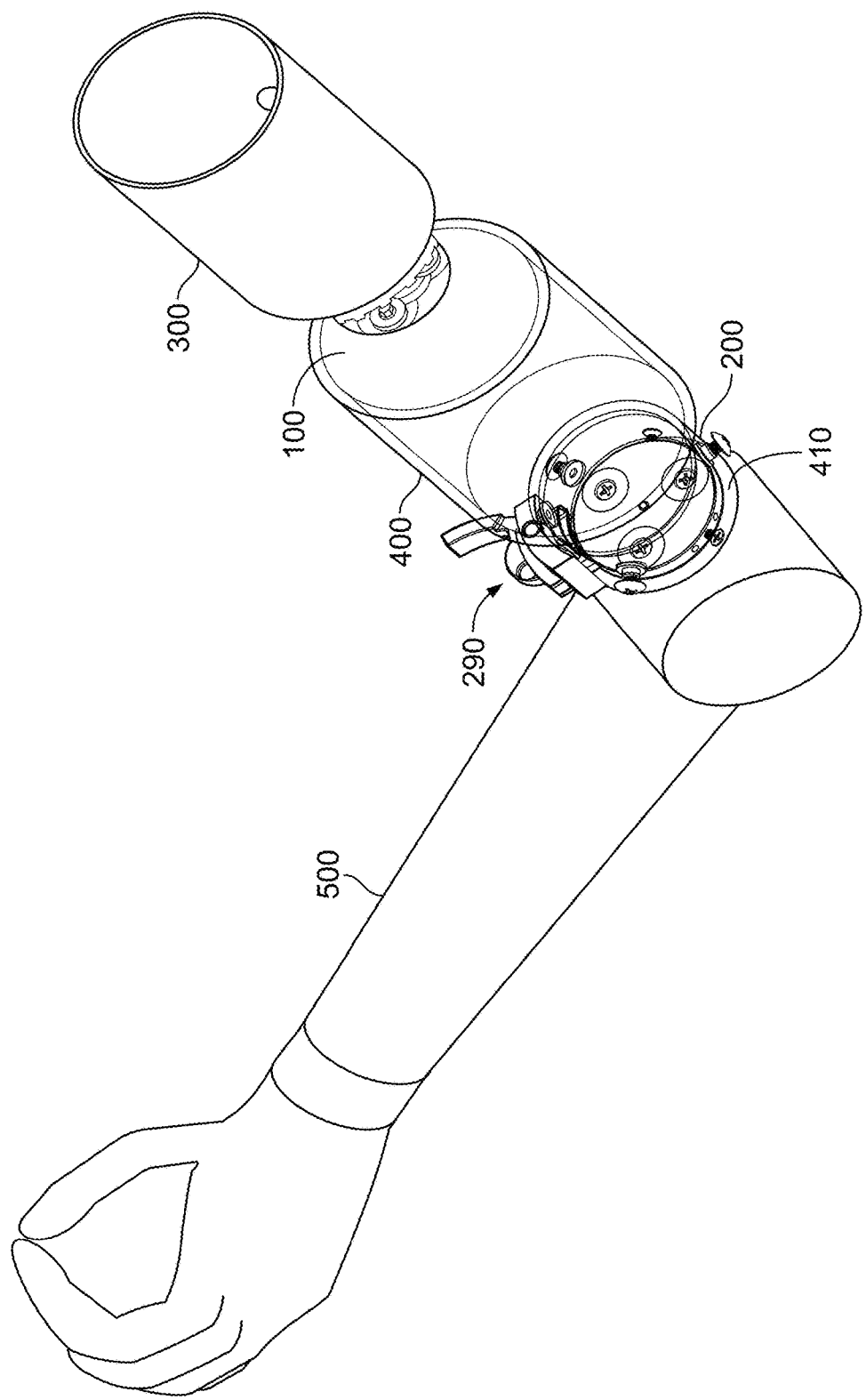
FIG. 1 shows an exploded view of one embodiment of a prosthesis system making use of proximal connector 100 and distal connector 200.

FIG. 1 is an exploded view of one embodiment of a prosthesis system making use of proximal connector 100 and distal connector 200. Proximal connector 100 is connected to liner 300, and together they can be inserted into hard socket 400. Assistive device 500, which is shown as a myoelectric prosthetic arm, is attached to hard socket 400 with a lamination collar 410.

Figure 2:
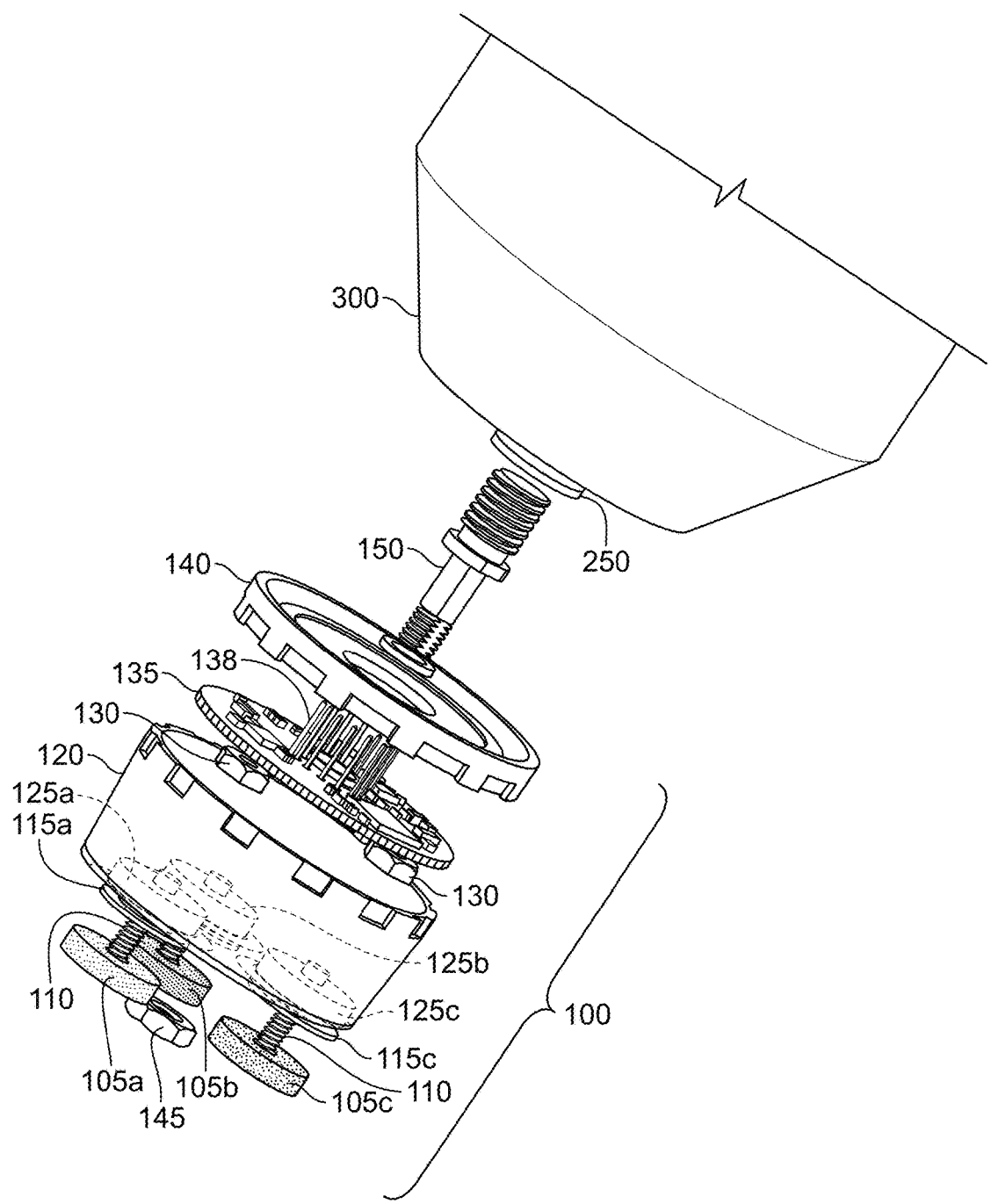
FIG. 2 shows an exploded orthographic view of one embodiment of proximal connector 100.

FIG. 2 shows an exploded side view of one embodiment of a proximal connector 100. Proximal connector 100 comprises a housing 120 having indentations 125*a*, 125*b*, and 125*c*. Generally speaking, we have found that proximal connector 100 is preferably no larger than the diameter of the user's residual limb. For instance, in a transhumeral location, the diameter of proximal connector 100 is preferably no larger than 2.5 inches, for the average user. Where proximal connector 100 is used to connect a lower limb prosthesis, it may be used just above the knee and is preferably no larger than four inches in diameter for the average user, and no larger than five inches in diameter for a larger user. Magnets 105*a*, 105*b*, and 105*c* may be inserted into indentations 125*a*, 125*b*, and 125*c*, respectively, and may be secured to housing 120 using screws 110 or other suitable attachment mechanisms. Compliance components 115*a*, 115*b* (not shown), and 115*c* may be fitted between magnets 105 and housing 120. In the embodiment shown in FIG. 2, compliance components 115 comprise of brass washers. Compliance components 115 provide compliance when the proximal connector 100 is attached to distal connector 200. Material other than brass washers could alternatively be used for compliance components 115 and include coiled springs, rubber dampers thin walled flexures, or other similar materials. The compliance component 115 behind each magnet 110 allows for a sustained electrical contact between proximal connector 100 and distal connector 200 even under external load forces and impulses, which could occur when the assistive device is bumped.

Figure 3:
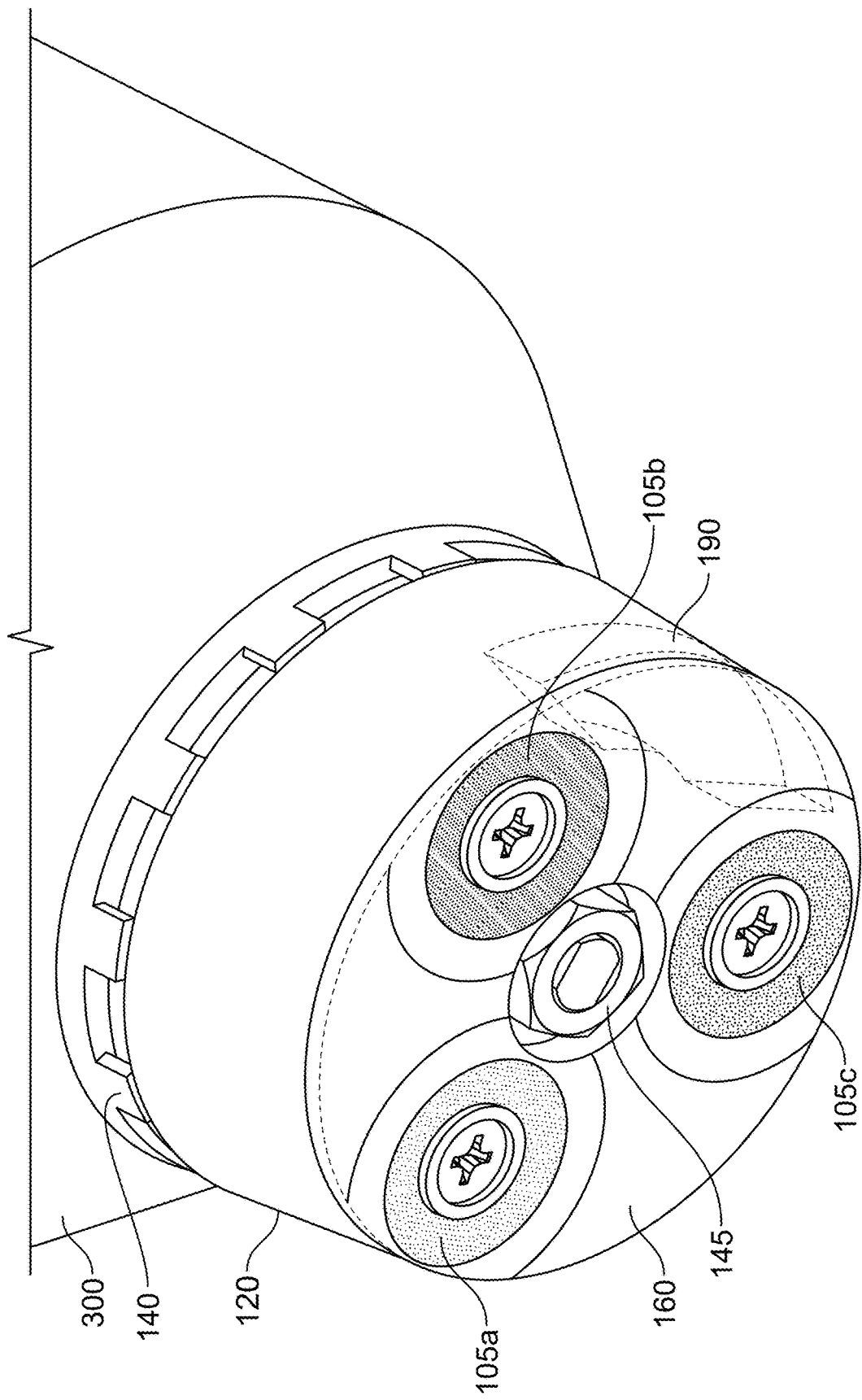
FIG. 3 shows an orthographic view of proximal connector 100.

Magnets 110 may be inserted into indentations 125 and are secured to housing 120 via screws 110 and nuts 130. As shown in FIG. 3, magnets 105*a*, 105*b*, and 105*c* may be arranged in a triangular configuration on face 160 of proximal connector 100. Face 160 is a planar surface. Two of the magnets 105 share a polarity and the third magnet 105 has a polarity opposite the other two. For example, magnets 105*a* and 105*b* may have a south facing polarity and magnet 105*c* has a north facing polarity. (Polarity direction is given with respect to face 160.) The configuration of the three magnets is such that two of the magnets share the same polarity and the third magnet has a polarity opposite the other two. The configuration is herein known as "alternating polarity."

Figure 4:
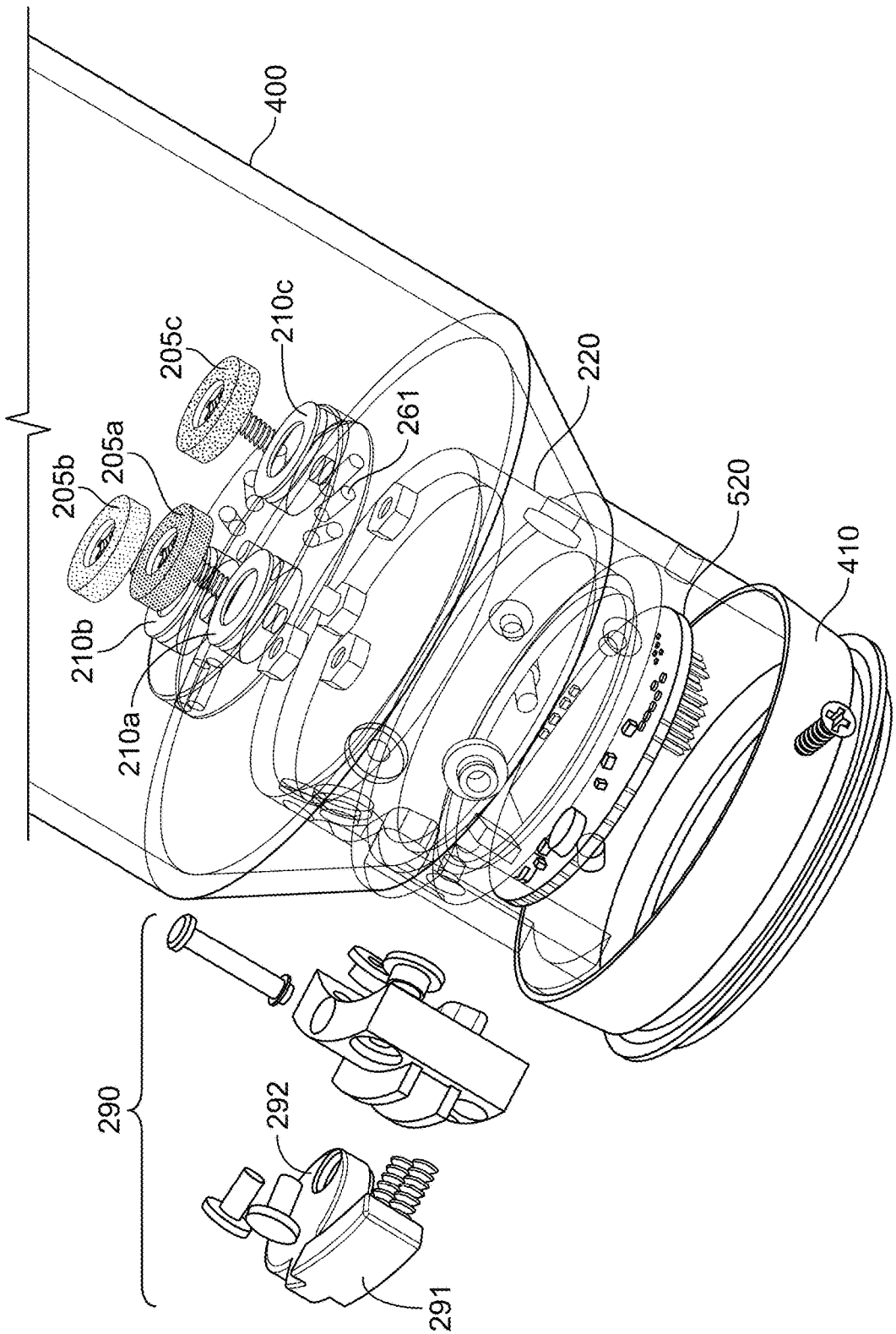
FIG. 4 shows an exploded orthographic view of distal connector 200.

FIG. 4 shows an exploded view of distal connector 200. Magnets 210*a*, 210*b*, and 210*c* can be inserted into indentations 225*a*, 225*b*, and 225*c*, respectively, and may be secured to housing 220 using screws 210 or other suitable attachment mechanisms. Compliance components 215*a*, 215*b*, and 215*c* may be fitted between magnets 210 and housing 220 and serve the same purpose as compliance components 115 used in proximal connector 100. Magnets 210 are also arranged in a triangular configuration having an alternating polarity, on face 260 of distal connector 200. Face 260 is a planar surface. Distal connector 200 may be attached to hard socket 400 by manufacturing the hard socket 400 with a cylindrical opening at its proximal end. The distal connector 200 can then be inserted and bolted into the cylindrical opening of hard socket 400 via bolts 410.

Figure 5:
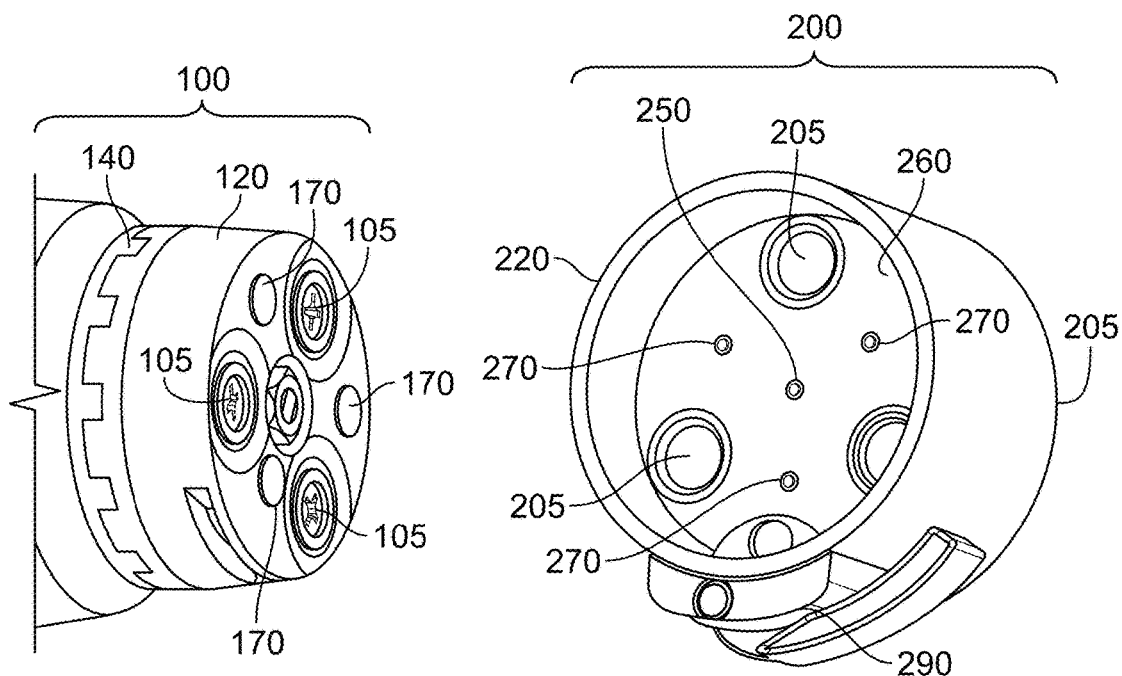
FIG. 5 shows orthographic views of proximal connector 100 and distal connector 200.

The proximal connector 100 may be coupled to a lid 140 that may be affixed to liner 300 using an adhesive, such as silicone, around the outer diameter edge. The lid 140 may be made from cured polymer resin or another suitable material. Lid 140 may be used to prevent sediment, liquids, or prosthesis user sweat from adversely affecting PCB 135 or other components of proximal connector 100. Lid 140 may utilize a keyed pattern, similar to the pattern in FIG. 2, that may be matched by a mating keyed pattern on housing 120. In one embodiment, the keyed pattern is a series of peaks and valleys, as shown in FIG. 5, that alternate around the circumference of lid 140. The keyed pattern locks lid 140 to housing 120 to further resist proximal connector 100 becoming unscrewed when applied with a torque force. Liner 300 may comprise thermoplastic elastomer (TPE), silicone, other elastomers, or other elastic plastics.

The magnetic force produced by the interaction of proximal connector 100 and distal connector 200 is created as follows. The user dons liner 300 over her residual limb. The user must don liner 300 over her residual limb in approximately the same position each time, within a variation of about 15 degrees, so that the liner is appropriately positioned on the residual limb. The user then brings hard socket 400 over liner 300. Once magnets 205 are sufficiently close in position to magnets 105, the corresponding magnetic force causes the magnets of a first polarity to become aligned with magnets of an opposite polarity to the first polarity. In the embodiment shown in FIG. 5, magnets 105*b* and 105*c* align with magnets 205*b* and 205*c*, and magnet 105*a* aligns with magnet 205*a*. The resulting alignment increases the magnetic force between proximal connector 100 and distal connector 200, causing proximal connector 100 and distal connector 200 to become magnetically attached. As a result, the hard socket 400 will snap into connection with liner 300. In this way, the user is able to attach liner 300 to hard socket 400 without needing to carefully line up the attachment mechanism of liner 300 with the attachment mechanism of hard socket 400 and without needing to see the two attachment mechanisms to make the attachment. Additionally, as magnets 105 and 205 align, the increasing magnetic force helps to snap hard socket 400 into connection with liner 300 without additional guidance from the user.

When the user is ready to remove (or "doff") the hard socket 400, the user pulls on hard socket 400 while rotating it relative to liner 300. Rotation of hard socket 400 causes distal connector 200 to rotate relative to proximal connector 100. The rotation causes the magnets of opposite polarity to become misaligned, thereby reducing the attractive force between magnets 105 and magnets 205. The reduced magnetic attraction allows the user to more easily remove hard socket 400.

In one embodiment, magnets 105 and 205 may be axial magnets. Magnets 105 and 205 may be made from Neodymium and can range in strength based on material grade (N38-N52) and shape (such as a disc, a cube, or other shape). The use of such high strength magnets provides a sufficiently strong attractive force without the need for a large magnet volume. For instance, in one example in which the area of contact of each Neodymium magnet was of material grade N42, with a ⅝ inches outer diameter (approximately 0.3 square inches) and was ⅛ inches thick, the magnetic force produced by the attraction of one of the magnets 105 and one of magnets 205 with opposite polarity is 31.8 Newtons (N), or 7.15 pounds of force. We have found that magnetic force as low as 20 N, and for certain patients lower, can be appropriate for a user. Different magnets providing different amounts of magnetic force could be used in other embodiments, for instance, in embodiments of the connectors that are used to couple two components of a lower prosthetic limb.

Proximal connector 100 and distal connector 200 each has exactly one magnet whose polarity opposes that of its other two magnets. As a result, when the user dons hard socket 400, proximal connector 100 and distal connector 200 will automatically align to a single rotational position in which the magnets of opposite polarity are matched up regardless of the starting rotational position of either connector 100 or 200.

The distal connector 200 may be approximately the size of, or smaller than, the distal end of a user's residual limb. In one embodiment, distal connector 200 is 2.25 inches in diameter for transhumeral amputations. Other appropriate sizes may be used. Distal connector 200 may be circular or cylindrical and may be made of plastic, such as a polymer resin, or another non-conductive material in order to allow electrical conduction at the appropriate points.

Distal connector 200 may further comprise anti-rotation lock 290 to physically lock proximal connector 100 to distal connector 200. The lock 290 would prevent an unwanted rotational force from unintentionally separating proximal connector 100 from distal connector 200. Hard socket 400 may comprise a window cutout that allows placement of latch onto distal connector 200.

Lock 290 may be made aluminum or another suitable material. In one embodiment, lock 290 comprises a cam mechanism 291 that rotates a flat circular disc 292 within the proximal connector 100 at slot opening 190. Lock 290 provides an extra physical locking mechanism when the proximal connector 100 and distal connector 200 are mated together. In one embodiment, the use of lock 290 may increase the loading to up to 200 lbs. of force. A push button, pin, or other latching mechanism could also provide a similar function to anti-rotation lock 290. To detach proximal connector 100 from distal connector 200, the user unlocks lock 290 and rotates the distal connector 200, either by rotating it directly or rotating the assistive device 500 or hard socket 400 to which distal connector 200 is coupled. This creates a rotational force that breaks the magnetic connection between magnets 105 and 215.

In one embodiment, face 260 of distal connector 200 is rotatable with respect to housing 220. When the assistive device system is first being prepared for the user by a prosthetist or other provider, it may be helpful for face 260 to be rotatable to correct for slight rotational misalignment of installation of the distal connector 200 within the hard socket 400. By enabling adjustable rotational settings of the face 260 with respect to the cylindrical axis of the distal connector 200, correct alignment is ensured of assistive device 500 relative to the user. Face 260 may be attached to housing 220 by screws that can be removed, allowing the provider to rotate face 260 to provide proper alignment. Face 260 is then reattached to housing 220 by screws using holes 261. It should be understood that the connector components are described as being made of polymer resin but any non-conductive material could be used.

Figure 6:
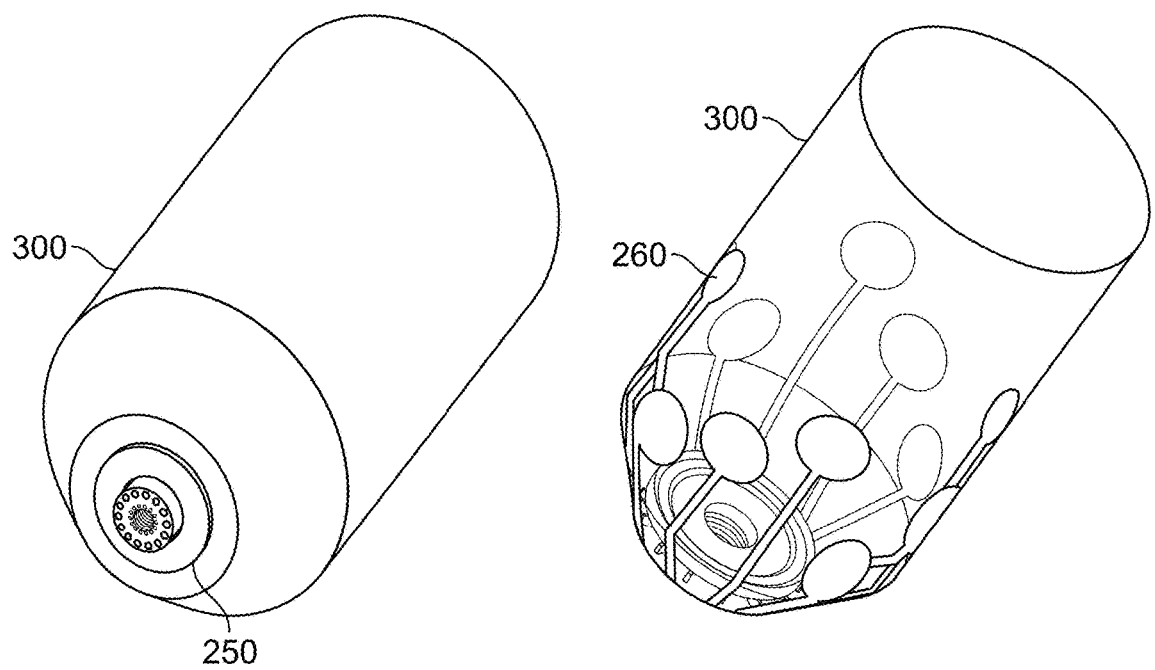
FIG. 6 shows two views of liner 300 having connector 250 and electrodes 260.

FIG. 6 displays a liner assembly for a residual limb. In one embodiment, the liner assembly comprises a non-conductive, gel (suspension) liner 300 that may be fitted tightly to a residual limb of a user. Liner 300 may incorporate any number of embedded electrodes. The liner includes electrodes, which may comprise metal domes, conductive fabric domes, or domes of other suitable conductive material to contact the residual limb. Liner 300 is attached to a centrally routed connector 250. Connector 250 may be machined from a plastic material that can withstand being embedded with the gel of liner 300 during high temperature and pressure fabrication. A press fit brass grommet around the protruding inner hub of connector 250 reinforces the attachment between liner 300 and connector 250. FIG. 6 displays a transparent view of liner 300. The figure shows connector 250 having a protruding inner hub and an outer flange to connect the embedded electrodes 260. Electrodes 260 may be embedded in liner 300. Electrodes 260 may be connected distally to connector 250 using female connector pins (not shown), which are attached to the distal end of electrodes 260 and inserted into holes of the inner hub within connector 250.

A signal acquisition printed circuit board (PCB) 135, also shown in FIG. 2, may be at least partially enclosed in housing 120 of proximal connector 100. Housing 120 may be configured to at least partially enclose PCB 135 by providing an opening in which PCB 135 may be placed. PCB 135 may have male connector pins 138 that insert into the ring of female electrical connector holes of connector 250, electrically connecting electrodes 260 to PCB 135 via connector 250. Center bolt 150 is threaded and secured into the distal end of connector 250 for physical attachment of the proximal connector 100. At the distal end of the center bolt 150 is a "Double-D" geometric pattern in which two parallel faces are machined flat along the length of center bolt 150 to allow for orientation alignment of proximal connector 100 and liner 300 and the corresponding embedded electrodes 260. Center bolt 150 may be secured to connector 250 with adhesive, so that it does not become unscrewed when applied with a torque force. The center bolt 150 is secured to proximal connector 100 using nut 145 and held in orientation with respect to proximal connector 100 by the mating of its "Double-D" geometric pattern. The "Double-D" for the center bolt is said to align proximal connector 100 but any geometry with a designated orientation could suffice.

PCB 135 conditions multiple electromyography (EMG) signals received from the user's residual limb by electrodes 260 and transmits them via standard controller area network (CAN) connector 137. PCB 135 may comprise an electronics electromyography (EMG) data acquisition system. In one embodiment, PCB 135 receives one or more analog EMG signals for conditioning. Said conditioning may comprise analog-to-digital conversion. Following acquisition, the signals may be filtered and amplified, then transmitted across a two-conductor controller area network (CAN) connector 137.

Figure 7:
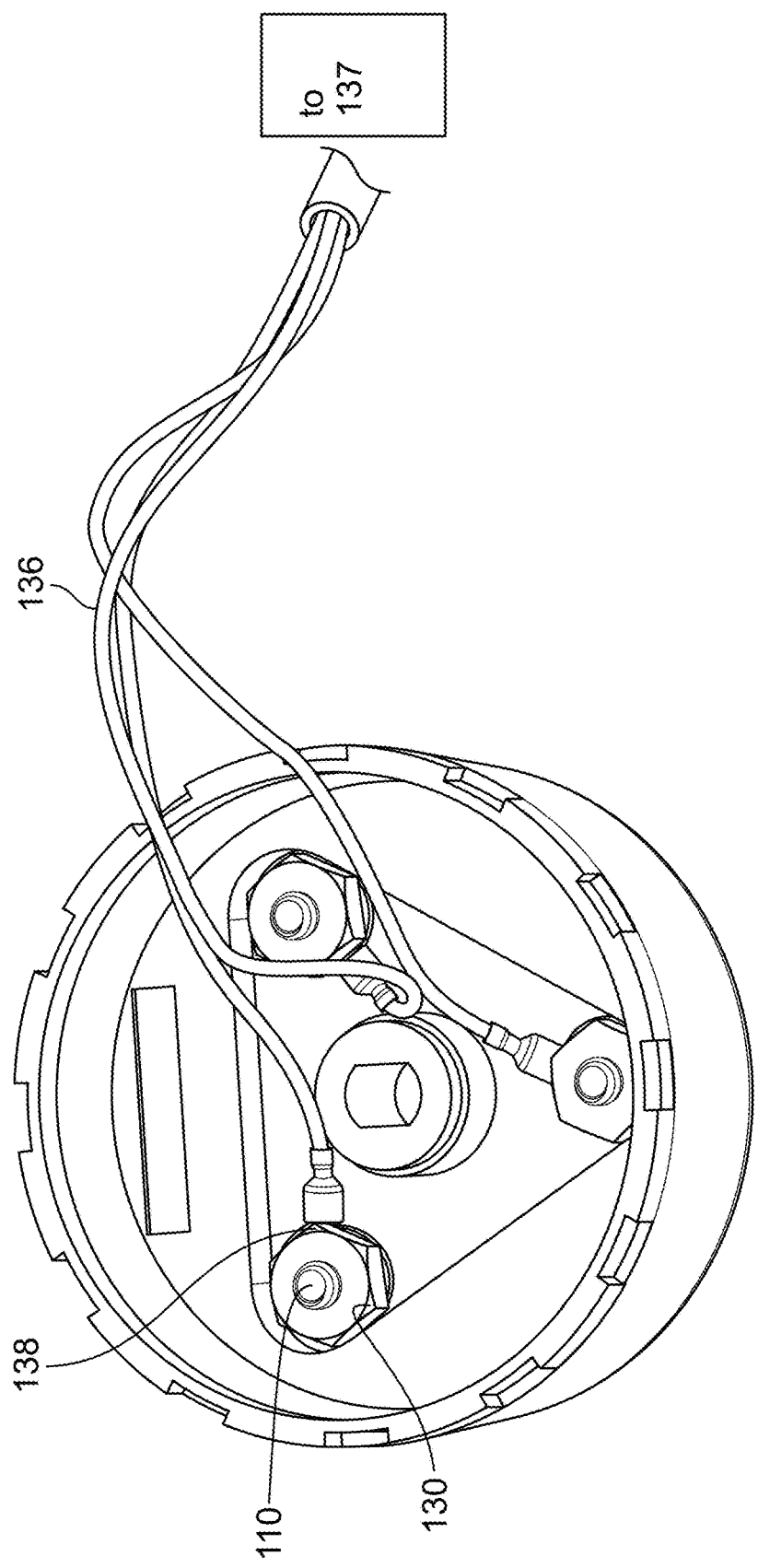
FIG. 7 shows a view of wiring harness 136 connecting PCB 135 to proximal connector 100.

In one embodiment, shown in FIG. 7, power and signal lines are routed to and from PCB 135 using a wiring harness 136 attached to CAN connector 137. Wiring harness 136 is attached using conductive metal eyelets 138 and secured against the interior side of proximal connector 100 to provide connections for power, electrical ground, signal high, and signal low. The metal eyelets 138 may be placed over screws 110 and clamped down with nuts 130. Metal eyelets 138 may be electrically insulated with electrical tape or other methods. Other methods of transmitting the electrical signals are also known. It should be understood that a similar wiring configuration may be used to receive signals transmitted to distal connector 200 and to transmit them to assistive device 500.

The PCB 135 may condition EMG signals received from the user and produce at least one signal that is representative of such EMG signals. In one embodiment, PCB 135 may transmit a signal high and a signal low that is representative of EMG signals from the user. Electrical signals indicating power, electrical ground, signal high, and signal low may transmit between CAN connector 137 and an electrical component exterior to the proximal connector 100. For instance, the electrical component exterior to proximal connector 100 may be the assistive device 500. It should be clear to one of ordinary skill in the art that different electrical connection components may be used in addition to or in lieu of CAN connector 137. Once face 160 and face 260 are in contact, resulting in magnetic attachment of proximal connector 100 and distal connector 200, electrical signals may be transmitted through magnets 105 and 205. These electrical signals may be representative of one or more signals generated by the muscles in the user's residual limb, and may be used to control assistive device 500. For example, EMG signals from the patient's residual limb may be detected by electrodes 260 and transmitted to PCB 135, where they are amplified and conditioned. PCB 135 outputs a signal high and a signal low, which are transmitted from magnets 105 and screws 110 to magnets 205 and screws 210. From there, the signals are further transmitted by wiring or other known systems to assistive device 500, where they are used to control the assistive device 500. In one embodiment, assistive device 500 comprises controller 520, which is connected by a wiring harness to magnets 205 and screws 210 of distal connector 200. Controller 520 may be electrically connected to assistive device 500 by wired means. Controller 520 may be external to housing 220 or may be fitted within housing 220. In one embodiment, controller 520 receives the signal high, signal low, and ground, and provides the power signal to PCB 135.

In one embodiment, screws 110 connect magnets 105 to proximal connector 100. Screws 110 provide part of a conductive path that allows electrical signals to be exchanged between the CAN connector 137 and an exterior electrical component, such as assistive device 500. Screws 110 may have a nickel coating, a steel cup casing, or other suitable conductive material.

An electrical ground signal is provided through direct contact between center bolt 150 and PCB 135. Distal connector 200 may further comprise an electrical spring pin 250, or another flexible conductive material, that makes contact with the distal end of center bolt 150 when faces 160 and 260 are in contact. Contact between spring pin 250 and center bolt 150 provides an electrical connection with the electrical ground.

Certain embodiments of proximal connector 100 and distal connector 200 may include other features that make it simpler for the user to don or doff the hard socket 400. In one embodiment, the exterior of housing 120 and the interior of housing 220 are each tapered at an angle allowing proximal connector 100 to be inserted more easily into distal connector 200. The taper may be 5 degrees from vertical or another appropriate angle to guide proximal connector 100 into distal connector 200. Additionally, the housings 120 and 220 may be sized such that a gap tolerance exists between the exterior of housing 120 and the interior of housing 220 when the proximal connector 100 and distal connector 200 are attached. One possible gap tolerance is 0.5 mm.

In another embodiment, other components of proximal connector 100 and distal connector 200 may provide the required electrical connection. FIG. 5 shows conductive screws 170 connected to proximal connector 100 and spring pins 270 connected to distal connector 200. When face 160 attaches to face 260 via magnetic force, electrical signals are passed between conductive screws 170 and electrical pins 270.

The words "screw," "bolt," and "nut" are used to describe exemplary embodiments and it should be understood that other fasteners with similar properties could alternately be used. The term "CAN" is used to describe an exemplary bus and it should be understood that other communication methods known in the art, such as other buses, could alternately be used.

The following are features and aspects of certain embodiments of the systems described herein, and are not intended to limit the scope of the claims.

One feature of certain embodiments described herein is ensuring continued mechanical and electrical attachment of the hard socket and myoelectric prosthesis to the liner The mechanical and electrical attachment should not be broken under the weight of the myoelectric prosthesis or under the weight of force or torque applied to the myoelectric prosthesis. Another feature of certain embodiments described herein is the transmission of electrical signals from EMG sensors within the liner to a microprocessor in the myoelectric prosthesis. Another feature of certain embodiments herein is transmission of power from the battery in the assistive device to a controller housed in the proximal connector. Another feature of certain embodiments described herein is the magnetic force provided by magnets of the proximal connector and distal connector, which provides a strong attractive force that holds an assistive device in place. The magnetic force also provides a weak rotational resistive force that allows a user to easily detach the assistive device from the user's liner when asserting a relative torque. Another feature of certain embodiments described herein is the connector magnets, which provide a force that guides distal connector 200 into proximal connector 100 once the connectors are in sufficiently close proximity, which assists in coupling the hard socket and the assistive device to the liner.

In other embodiments, proximal connector 100 and distal connector 200 may be oval shaped, which may provide more surface area on faces 160 and 260 for different magnets 105 and 205. In this embodiment, distal connector 200 could not rotate into alignment with proximal connector 100. However, such an embodiment could provide a different attractive and repulsive force due to magnets 105 and 205.

The proximal connector 100 and distal connector 200 are configured such that their assembly is compact and sized appropriately for use in an assistive device system. Although the proximal connector 100 and distal connector 200 are described in most detail with respect to their use in connecting liner 300 to hard socket 400, other uses of proximal connector 100 and distal connector 200 should be apparent. For example, proximal connector 100 and distal connector 200 may be used to connect two components of an assistive device. For example, connectors 100 and 200 could be utilized in a suspension system for a prosthetic leg in order to attach one prosthetic leg component to another prosthetic leg component. When used with stronger magnets, the proximal connector and distal connector can have valuable applications in industries such as manufacturing or transportation where there is a need to connect two objects with a strong magnetic force, disconnect them with a relatively weak rotational force and optionally allow for transmission of one or more electric signals. Alternatively, the connector could be used with weaker magnets in learning kits or toy kits having multiple links for connection.

What is claimed is:

1. A system for attaching an assistive device to a limb, the system comprising:
   a. a liner having an opening for insertion of a limb;
   b. a proximal connector attached to the liner, the proximal connector having a distal planar surface;
   c. a plurality of proximal magnets arranged on the proximal connector at the distal planar surface of the proximal connector;
   d. a distal connector having a proximal planar surface;
   e. a plurality of distal magnets arranged on the distal connector at the proximal planar surface of the distal connector; and
   f. a plurality of compliance components configured for compliance under load;
   wherein each of the compliance components is fitted behind one of the proximal magnets or behind one of the distal magnets such that a proximal or distal magnet is located between each compliance component and a respective planar connector surface; and
   wherein at least one signal that is representative of one or more electromyography signals can be transmitted between the proximal connector and the distal connector via at least one of the plurality of the proximal magnets and at least one of the plurality of distal magnets when the proximal connector and the distal connector are magnetically attached.

2. The system of 1, wherein the plurality of proximal magnets are configured in an alternating polarity on the proximal connector and the plurality of distal magnets are configured in an alternating polarity on the distal connector.

3. The system of claim 1, wherein the proximal connector allows for at least partial enclosure of a circuit board.

4. The system of claim 3, further comprising a circuit board for conversion of the one or more electromyography signals.

5. The system of claim 1, wherein a magnetic force produced by the attraction of one of the plurality of proximal magnets and one of the plurality of distal magnets is at least 20 N of force.

6. The system of claim 1, wherein proximal connector has a diameter no greater than about 2.5 inches.

7. The system of claim 1, wherein the proximal connector has a diameter greater than about 2.5 inches and not greater than about 5 inches.

8. The system of claim 1, wherein the proximal connector and the distal connector are each mechanically sized so that a gap exists between the interior of one of said connectors and the exterior of the other of said connectors when the proximal connector and the distal connector are magnetically attached.

9. The system of claim 1, wherein the at least two signals that are representative of one or more electromyography signals can be transmitted between the proximal connector and the distal connector via at least two of the plurality of the proximal magnets and at least two of the plurality of distal magnets when the proximal connector and the distal connector are magnetically attached.

10. The system of claim 1, wherein the liner comprises a gel liner.

11. The system of claim 1, wherein the proximal planar surface of the distal connector is rotatable about a cylindrical axis of the distal connector.

12. The system of claim 1, wherein the distal planar surface of the proximal connector and the proximal planar surface of the distal connector permit rotation between the distal connector and the proximal connector.

13. The system of claim 1, wherein:
   the proximal connector and the distal connector are magnetically attached when the proximal magnets and the distal magnets are in contact and aligned;
   the proximal magnets and the distal magnets are configured to exert a first attractive force when the proximal magnets and the distal magnets are in contact and aligned, the distal connector is rotatable with respect to the proximal connector to reduce the attractive force exerted between the proximal magnets and the distal magnets to facilitate removal of the distal connector from the proximal connector; and
   the proximal magnets and the proximal connector form the distal planar surface of the proximal connector and the distal magnets and the distal connector form the proximal planar surface of the distal connector, and the planar surfaces are in contact when the proximal magnets and the distal magnets are in contact and aligned.

14. A system for attaching an assistive device to a limb, the system comprising:
   a. a liner, having an opening for the insertion of a limb;
   b. a proximal connector attached to the liner, the proximal connector comprising a proximal housing;
   c. a plurality of proximal magnets arranged on the proximal housing;
   d. a distal connector comprising a distal housing, wherein the distal housing and the proximal housing are each tapered; and
   e. a plurality of distal magnets arranged on the distal housing;
   wherein at least one signal that is representative of one or more electromyography signals can be transmitted between the proximal connector and the distal connector via at least one of the plurality of the proximal magnets and at least one of the plurality of distal magnets when the proximal connector and the distal connector are magnetically attached.

15. The system of claim 14, wherein the plurality of proximal magnets are configured in an alternating polarity on the proximal housing and the plurality of distal magnets are configured in an alternating polarity on the distal housing.

16. The system of claim 14, wherein the proximal housing allows for at least partial enclosure of a circuit board.

17. The system of claim 14, wherein a magnetic force produced by the attraction of one of the plurality of proximal magnets and one of the plurality of distal magnets is at least 20 N of force.

18. The system of claim 14, wherein the proximal connector has a diameter not greater than about 2.5 inches.

19. The system of claim 14, wherein the proximal connector has a diameter greater than about 2.5 inches and not greater than about 5 inches.

20. The system of claim 14, further comprising a circuit board for conversion of the one or more electromyography signals.

21. The system of claim 14, wherein the proximal housing and the distal housing are each mechanically sized so that a gap exists between the interior of one of said housings and the exterior of the other of said housings when the proximal connector and the distal connector are magnetically attached.

22. The system of claim 14, wherein the at least two signals that are representative of one or more electromyography signals can be transmitted between the proximal connector and the distal connector via at least two of the plurality of the proximal magnets and at least two of the plurality of distal magnets when the proximal connector and the distal connector are magnetically attached.

23. The system of claim 14, wherein the liner comprises a gel liner.

24. The system of claim 14, wherein the distal connector has a proximal face and the plurality of distal magnets are arranged on the proximal face of the distal connector.

25. The system of claim 24, wherein the proximal face of the distal connector is rotatable about a cylindrical axis of the distal connector.

* * * * *